United States Patent [19]

Kientzler

[11] Patent Number: Plant 7,476

[45] Date of Patent: Mar. 19, 1991

[54] IMPATIENS PLANT NAMED THECLA

[75] Inventor: Ludwig Kientzler, Gensingen, Fed. Rep. of Germany

[73] Assignee: Paul Ecke Ranch, Encinitas, Calif.

[21] Appl. No.: 394,748

[22] Filed: Aug. 16, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A new and distinct cultivar of Impatiens plant named Thecla characterized by its large, bright dark pink flowers; early, continuous and prolific flowering, dark reddish-green foliage, and excellent self-branching, giving the plant a full yet erect appearance.

1 Drawing Sheet

The present invention relates to a new and distinctive cultivar of Impatiens plant, botanically known as Impatiens, and known by the cultivar name Thecla. The new cultivar was developed by me in Gensingen, Federal Republic of Germany through controlled breeding by crossing male and female parents which are unknown at this time.

Asexual reproduction by terminal cuttings taken at Gensingen, Federal Republic of Germany, has shown that the unique features of this new impatiens are stabilized and are reproduced true to type in successive propagations.

The following characteristics distinguish the new impatiens from both its parent varieties and other cultivated impatiens of this type known and used in the floriculture industry.

(1) Large, bright, dark pink flowers.

(2) Early and prolific flowering, with the flowers being long-lasting and flowering continuously.

(3) Dark reddish-green foliage.

(4) Excellent self-branching habit gives the plant a full appearance, yet erect and somewhat spreading.

The accompanying colored photograph is a top perspective view of the new cultivar, showing color as true as it is reasonably possible to obtain in a colored reproduction of this type.

The following is a detailed description of my new impatiens cultivar based on plants produced under commercial practice in Encinitas, Calif. The described characteristics were noted between December 10–20 and were based on unrooted cuttings rooted under intermittent mist and then transplanted into 6" pots, with flowering commencing in November. Color references are made to the Royal Horticultural Society Colour Chart (R.H.S.), except where general terms of ordinary dictionary significance are used.

Parentage:

A. *Type cutting.*—Tip, with stems 2–3 cm long developing to 4–5 cm after 21 days following propagation.

B. *Time to initiate roots.*—8–10 days at 23° C.; nicely developed root mass in 18–21 days.

C. *Rooting habit.*—Numerous, fibrous adventitious roots from the stem.

Plant description:

A. *Form.*—Symmetrical, bush shaped, flowering herb, with self-branching characteristics giving the plant a full appearance.

B. *Habit of growth.*—Vigorous, self-branching, medium habit, producing whorls of leaves and flowers on branched stems. Growth is indeterminate and flowering is continuous.

C. *Foliage description.*—Leaves are simple. Lower leaves on stem are opposite. Higher leaves in whorls of 3–5. (1) Leaf shape: elliptic to ovate, tip acuminate, base acute. (2) Leaf blade size: 8–10 cm long × 3.5–4.5 cm wide. (3) Leaf margin: ciliated and lightly serrated. (4) Leaf texture: (a) Upper surface: glabrous. (b) Under surface: glabrous. (5) Leaf color: dark green, with reddish veins and mid-vein. (a) Upper surface: near 147A. (b) Under surface: purplish-red, near 183B. (6) Venation: pinnate.

Flowering description:

(A) *Flowering habit.*—Very floriferous. Flowering is continuous. Flowers develop progressively around the whorl of leaves, taking 5–7 days from buds which show color, to bloom. Flowers are single and large, lasting for 2–3 weeks.

(B) *Natural flowering season.*—Flowering is indeterminate and occurs throughout the year. Quantity of flowers increases with increasing light intensity and duration.

(C) *Flower buds.*—Ellipsoidal and covered with 5 sepals. A reddish, approximately 5.0 cm long spur originates from the base of the major sepal. Two additional sepals occur on either side of the pedicel, superior to the major sepal.

(D) *Flowers borne.*—Singly, on pedicels 6 cm long; pedicels reddish in color.

(E) *Quantity of flowers.*—Floriferous. One or two flowers per leaf occurring progressively around the whorl of leaves so that tight buds to mature blooms are visible at the same time in large numbers.

(F) *Petals.*—(1) Number of petals: five (5). (2) Shape: Top petal heart shaped with wide base, all other petals heart shaped with pointed base. All petals overlap. (3) Color: bright, dark pink. (a) Upper surface: near 54A at center or eye, main surface area closest to 55A, and a lighter 55D at petal tips. (b) Under surface: near 55B. (4) Size of flowers: 5 cm across.

(G) *Reproductive organs.*—(1) Stamens: Five (5), with the lower stamen being shorter than the other stamens. Stamens are united in an asymmetrical tube surrounding the ovary. (2) Anthers: Hooded, cream fused with red. (3) Pollen: Cream color. (4) Stigma: Five pointed star, colorless. (5) Styles: Very short, reddish in color. (6) Ovary: 5 celled, 4–5 mm. long until fertilized, green in color.

(H) *Resistance to disease.*—Thecla has good resistance to the stem rotting organism Pythium, the root rotting organism Rhizotonia, and the gray mold Botrytis.

I claim:

1. A new and distinct cultivar of Impatiens plant named Thecla, as illustrated and described.

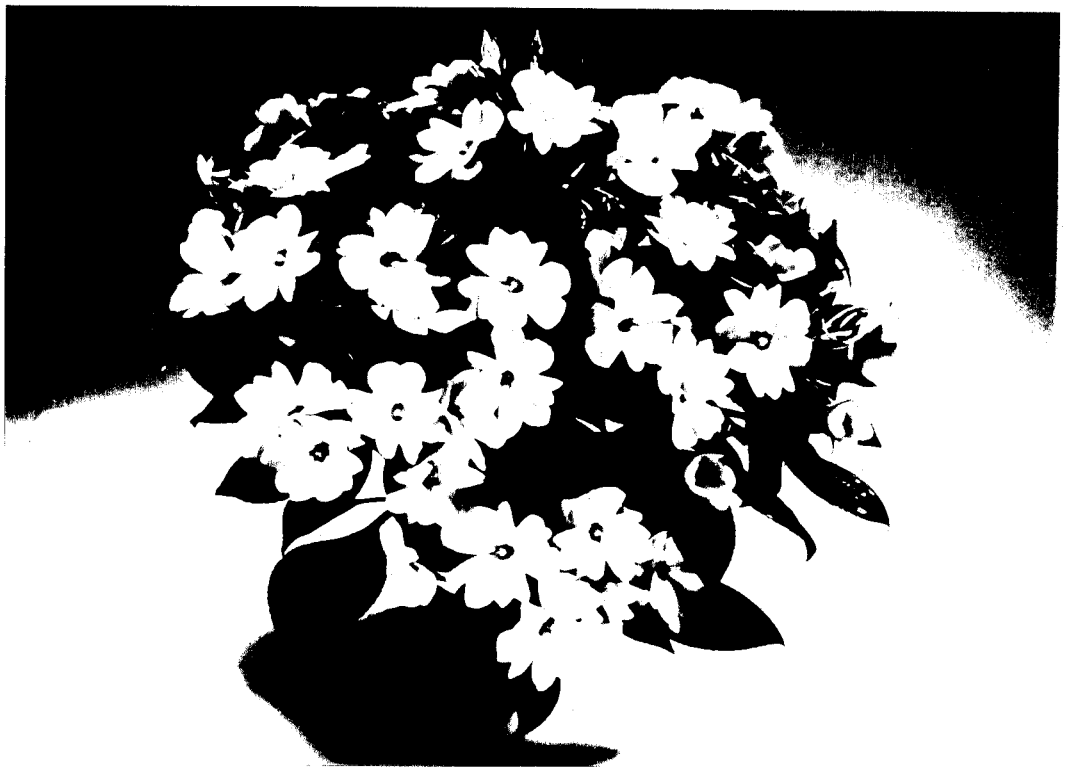

* * * * *